(12) United States Patent
Hubrich et al.

(10) Patent No.: US 6,658,359 B2
(45) Date of Patent: Dec. 2, 2003

(54) METHOD FOR DETERMINING THE VISCOSITY OF AN OPERATING LIQUID OF AN INTERNAL COMBUSTION ENGINE

(75) Inventors: Stefan Hubrich, Filderstadt (DE); Michael Pulvermueller, Deggingen (DE)

(73) Assignee: Conti Temic microelectronic GmbH, Nuremberg (DE)

( * ) Notice: Subject to any disclaimer, the term of this patent is extended or adjusted under 35 U.S.C. 154(b) by 0 days.

(21) Appl. No.: 10/146,765

(22) Filed: May 15, 2002

(65) Prior Publication Data

US 2002/0174712 A1 Nov. 28, 2002

(30) Foreign Application Priority Data

May 22, 2001 (DE) .......................... 101 24 888

(51) Int. Cl.$^7$ .......................... G01F 17/00; G01F 23/00
(52) U.S. Cl. .......................... 702/50; 73/54.25
(58) Field of Search ...................... 702/50.33; 73/54.01, 73/54.13, 54.25, 53.05

(56) References Cited

U.S. PATENT DOCUMENTS

| | | | | |
|---|---|---|---|---|
| 4,007,629 A | * | 2/1977 | Hochstein | .................. 73/53.05 |
| 4,277,971 A | | 7/1981 | Drzewiecki et al. | |
| 4,733,556 A | * | 3/1988 | Meitzler et al. | ........... 73/53.05 |
| 5,369,396 A | | 11/1994 | Kurata et al. | |
| 5,377,531 A | * | 1/1995 | Gomm | ...................... 73/53.05 |
| 6,463,796 B1 | * | 10/2002 | Van Mullekom et al. | .. 73/118.1 |

FOREIGN PATENT DOCUMENTS

| | | |
|---|---|---|
| DE | 4011448 | 10/1991 |
| DE | 4119437 | 12/1992 |
| DE | 4131969 | 4/1993 |
| DE | 4315519 | 11/1993 |
| DE | 19518776 | 11/1996 |
| GB | 1529051 | 10/1978 |
| JP | 10-260126 | 9/1998 |

* cited by examiner

Primary Examiner—John Barlow
Assistant Examiner—Demetrius R Pretlow
(74) Attorney, Agent, or Firm—W. F. Fasse; W. G. Fasse

(57) ABSTRACT

C9The invention relates to a method for determining the viscosity of an operating liquid of an internal combustion engine of a vehicle by establishing the level of the operating liquid.

In a known method, the viscosity of the operating liquid is established from the changes to the level in the operating liquid over a period of time. This viscosity is determined after turning off the internal combustion engine by measuring the variation of the engine oil level over a period of time. The measurement can, however, also take place exclusively after the internal combustion engine has been turned off.

In the present method, this disadvantage is avoided in that the level and the variation of the transverse acceleration are measured constantly in order to determine the viscosity of the operating liquid from the variation against time of the two signal curves.

The advantage of the invention is that sensor signals which are already available from proven series-production sensor arrangements are combined to also determine the viscosity as an additional parameter. The computations needed for this are performed by standard control units.

6 Claims, 3 Drawing Sheets

METHOD FOR DETERMINING THE VISCOSITY OF AN OPERATING LIQUID OF AN INTERNAL COMBUSTION ENGINE

FIELD OF THE INVENTION

The invention relates to a method for determining the viscosity of an operating liquid of an internal combustion engine.

BACKGROUND OF THE INVENTION

A method of this kind is known from DE 195 18 776 A1 which describes a method for establishing the viscosity of an operating liquid on the basis of the changes in the level of the operating liquid over a period of time. In this known method, the viscosity of the engine oil is determined after having turned off an internal combustion engine by measuring the variation of the engine oil level over a period of time. The return of the engine oil to the sump after the engine has been turned off takes place with a time delay that depends on the viscosity. Apart from the variation of the level of the oil against time, the oil temperature is also a factor in the known method because the viscosity of the engine oil generally depends on its temperature.

Apart from these variables that are to be measured in a simple manner, the measurement of the viscosity in accordance with the known method is, however, also influenced by other variables. For instance, a high dynamic loading of the internal combustion engine over a period of time immediately before it is turned off can lead to foaming of the engine oil. The consequent slower change in level after turning the engine off results in corruption of the actual measurement. An objective measured variable for the dynamic loading of the internal combustion engine cannot, however, be determined in a simple manner.

Furthermore, when the internal combustion engine is turned off while the vehicle is in an inclined position, this also has an adverse effect on the return flow of the engine oil into the sump.

Another disadvantage is due to the fact that the electronic modules needed for the measurement still have to be actively operated for the required period of time after the internal combustion engine has been turned off.

The object of the invention is to specify a method for determining the viscosity of an operating liquid of an internal combustion engine by measuring the level of said liquid, whereby the method supplies a precise result with few measured variables and is performed while the internal combustion engine is in operation.

This object is solved by a method having the features according to the present invention as described and claimed herein.

SUMMARY OF THE INVENTION

In the method for determining the viscosity of an operating liquid of an internal combustion engine of a vehicle, initially a first signal is acquired corresponding to the variation against time of the level and then a second signal is acquired corresponding to the variation against time of the state of the vehicle that has an influence on the measured level of the operating liquid. The first and the second signals are then fed to a filter that allows the signals to be analyzed with respect to their dynamic response. This results in a third signal and a fourth signal being generated, where the third signal is the result of filtering the first signal and the fourth signal is the result of filtering the second signal. The fourth signal is then compared with a threshold value and a ratio relating the fourth signal to the third signal is formed according to the result of the comparison. The mean value over a multiple number of values of the ratio of the fourth to the third signal corresponds to the viscosity of the operating liquid.

The advantage of the invention is that sensor signals that are already available from sensor arrangements which have been tried out in practice and are in standard production can be combined with each other and from this the viscosity can be determined as an additional parameter. The necessary computation is performed by standard control devices.

In an advantageous form of embodiment of the method, the transverse acceleration of the vehicle is measured as the second signal. The continuous measuring signal of the oil level sensor is gated with the continuous signal of the transverse acceleration sensor. The result leads to a statement on the viscosity of the oil. Transverse accelerations are measured regularly for other systems such as for example, ESP.

Acquisition of the measured values of the first and second signals is performed preferably at a rate of approximately 1 to 1.5/s. This rate of measurement is the viscosity and small enough to avoid generating enough to provide reliable information relating to excessively large volumes of data.

For filtering the first or the second signal, preferably a floating standard deviation is formed from a first quantity of values. The third or fourth signals respectively form the output of the filter. The floating standard deviation uses relatively simple statistical methods to provide good information on the dynamic response of the signals.

The number of values for determining the floating standard deviation here is in the range from 5 to 100. A value of 15 has been found in a series of measurements to be particularly advantageous.

The generation of the mean value of the ratio of the fourth signal to the third signal is effected advantageously over approximately 50 to 300 values.

The invention will now be described with reference to the examples of embodiment and the figures.

DETAILED DESCRIPTION OF THE INVENTION

A particularly advantageous embodiment of the method relates to the determination of the viscosity of the oil in a motor vehicle engine.

The Temic QLT oil level sensor currently manufactured as a standard product supplies a continuous oil level signal.

The information on the momentary transverse acceleration is supplied by a transverse acceleration sensor belonging to the ESP or chassis control system.

Because of the movement of the oil in the oil sump, the oil level signal varies according to the current situation when travelling. Particularly when transverse accelerations occur, the centrifugal force results in different momentary oil levels on the two sides of the oil sump. These dynamic level differences become more noticeable as the viscosity decreases (lower viscosity), i.e. high-viscosity oil reveals less marked level differences when travelling in a curve than low-viscosity oil. If one collects the information from both sensors, for instance in the motor control unit, it is now possible to relate the change in oil level to the transverse acceleration and consequently to deduce the viscosity of the oil. By utilizing the sensor signals supplied in the vehicle by the transverse acceleration sensor and the QLT oil level sensor, it is possible to determine an additional quality parameter (=viscosity) that could not previously be measured.

Figure 1:
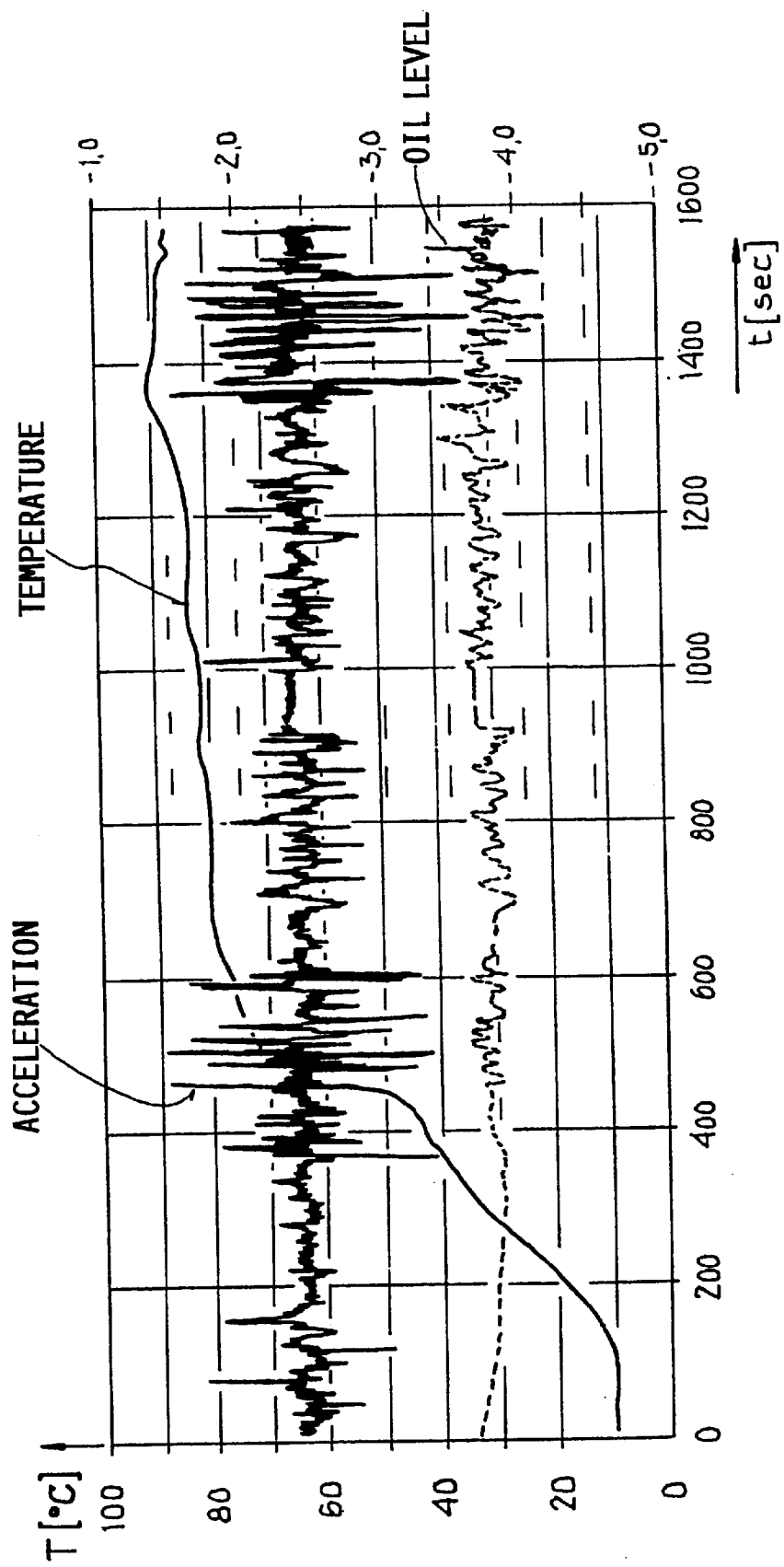
FIG. 1 shows a diagram with the variation against time of oil temperature, transverse acceleration and oil level on a test trip.

FIG. 1 shows a diagram with the variation against time of oil temperature, transverse acceleration and oil level during a test trip. At the beginning of measurement, one can see that at low temperatures the viscosity of the engine oil is still so high that even large transverse accelerations have only a scarcely perceptible influence on the measured oil level. This influence becomes increasingly greater as the temperature of the engine oil rises and is then finally clearly pronounced at normal operating temperature.

In order to now set the two signals in relation to each other, they are first fed into a filter which supplies as a result a measure for the dynamic response of the two signals. A filter in this context is understood to mean quite generally any signal conditioning element which allows evaluation with respect to the dynamic response.

Figure 2:
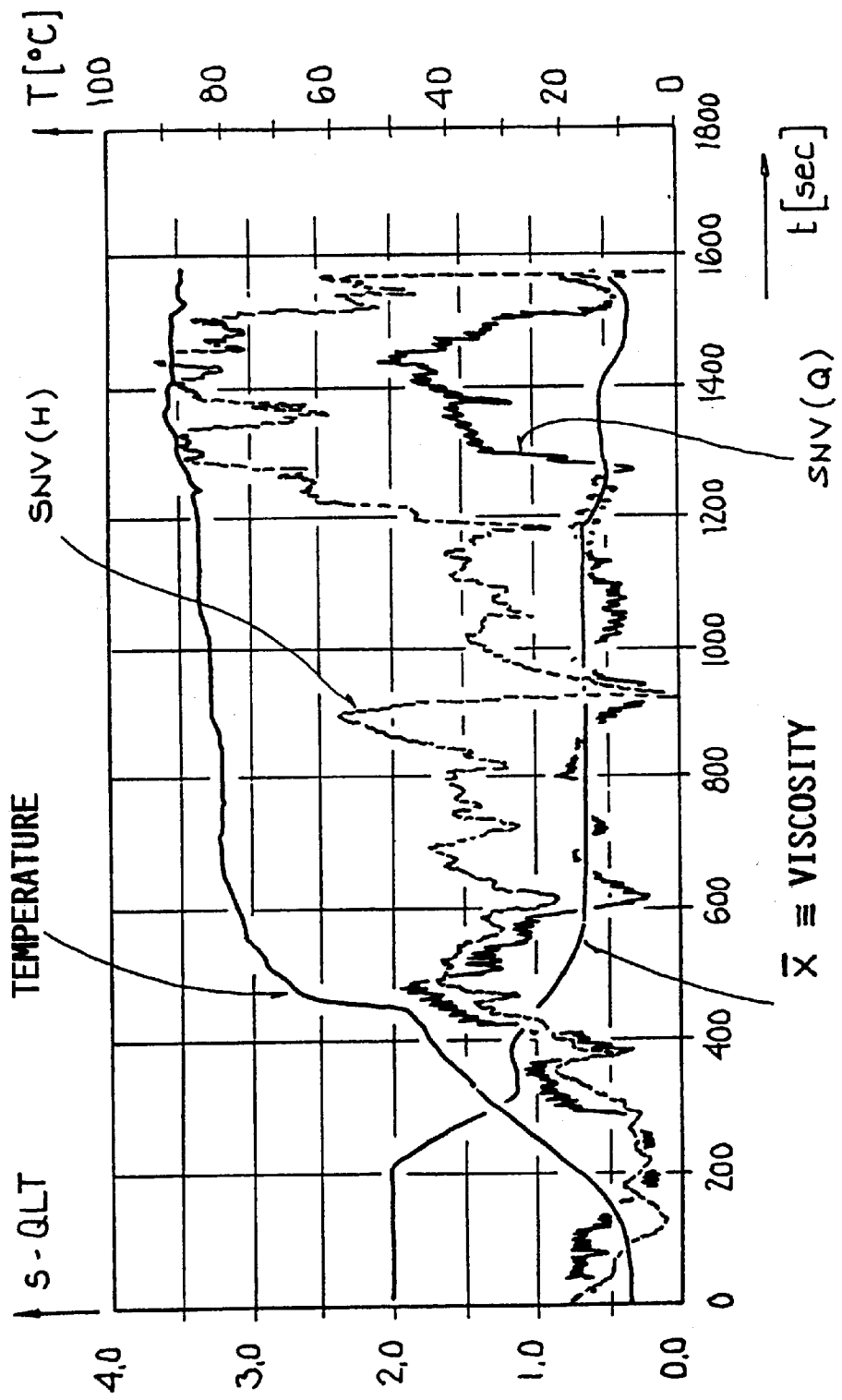
FIG. 2 shows a diagram with variation against time of oil temperature, SNV(Q), SNV(H) and the viscosity X measured on the test trip.

The floating standard normal distribution SNV over a fixed number of measured values has been found advantageous. The curves for the appropriately filtered signals of transverse acceleration SNV(Q) and the measured oil level SNV(H) have been entered in FIG. 2 similarly to FIG. 1.

The filtered signals are then set in relation to one another as soon as the value for the signal whose magnitude is originally responsible for the change in the oil level—in the present case the transverse acceleration—is above a preset threshold value K. The mean value over a multiple number of these ratios essentially corresponds to the viscosity of the engine oil.

Figure 3:
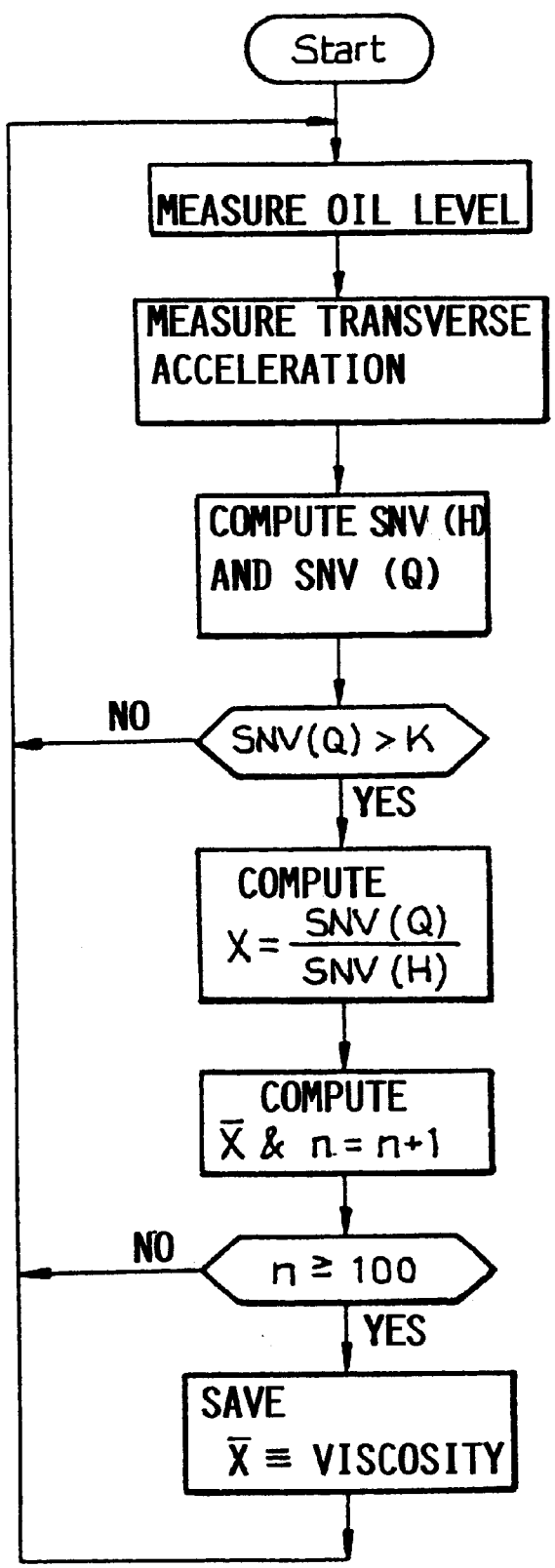
FIG. 3 shows a flowchart of the method.

FIG. 3 shows a flowchart for the method. First of all, the oil level H and the transverse acceleration Q are measured. It has been found here to be sufficient if the signals or the acquisition of the measured values are sampled at a rate of approx. 1 to 1.5/s. The floating standard normal distribution SNV for both signals SNV(Q), SNV(H) is then computed over a preset number of n values. The number n=15 has been found to be advantageous here. In practice, it is possible to select n from a wide range of between approx. 5 and 100, depending on the application. The floating standard normal distribution for the transverse acceleration SNV(Q) is then compared with a threshold value K. If the threshold value K is not exceeded, a return is made to the start of the method; if the threshold value K is exceeded, the quotient X=SNV(Q)/SNV(H) is computed. If values for X were previously established, the mean value $\overline{X}$ is computed. As soon as the mean value $\overline{X}$ has been generated over a sufficiently high number of single values, it can be used as parameter for the viscosity. In the flowchart in FIG. 3, this is illustrated by way of a counting variable that must reach the value 100 before the mean value $\overline{X}$ is saved as parameter for viscosity of the engine oil.

The calculation of the viscosity can also be effected through a suitable arrangement directly in the oil level sensor provided it is possible to also access the data from the acceleration sensor. In the normal case, the data is acquired and evaluated in a central control unit. Finally, the computed viscosity value is sent through an interface to a diagnostic unit or it is evaluated by an onboard diagnostic device in the vehicle.

In addition to the transverse acceleration, a number of alternative quantities can be taken into account in order to determine the viscosity, as long as they have just one effect on the measured operating liquid level. Thus, for example, the longitudinal acceleration or the engine speed can also be used as output variable in place of the transverse acceleration. Both variables cause a change to the level of the engine oil, their influence on the change being again dependent on the viscosity. When using the signal for the longitudinal acceleration, the measured oil level is influenced by movement of the oil in the oil sump, similarly to the transverse acceleration. When using the signal for the engine speed as output variable, use can be made of the fact that the volume of oil in the oil circuit varies according to the engine speed. It is simply necessary to adjust the signal acquisition and the measurement and filter parameters in order to also determine the viscosity of the oil from these parameters in a similar way.

What we claim is:

1. A method for determining the viscosity of an operating liquid of an internal combustion engine of a vehicle by establishing a measured level of the operating liquid, comprising the following steps:

acquiring a first signal that corresponds to a variation against time of the measured level, acquiring a second signal that corresponds to a variation against time of a state of the vehicle that has an influence on the measured level of the operating liquid, feeding the first and second signals to a filter and filtering the first and second signals to allow the first and second signals to be analyzed with respect to the dynamic response thereof, resulting in a third signal and a fourth signal being generated, comparing the fourth signal with a threshold value, and forming a ratio relating the fourth signal to the third signal according to a result of the comparing, and determining a mean value over a plural number of values of the ratio, wherein the mean value corresponds to the viscosity of the operating liquid.

2. The method in accordance with claim 1 wherein the step of acquiring the second signal comprises measuring the transverse acceleration of the vehicle as the second signal.

3. The method in accordance with claim 1, wherein the acquiring of the first and second signals comprises respectively acquiring measured values at a rate of 1 to 1.5/s.

4. The method in accordance with claim 1, wherein the filtering comprises forming a floating standard deviation from a number of values of the first signal or the second signal respectively, and wherein the floating standard deviation forms the output of the filter as the third signal or the fourth signal respectively.

5. The method in accordance with claim 4, wherein the number of values for forming the floating standard deviation is in a range from 5 to 100.

6. The method in accordance with claim 1, wherein the plural number of values for determining the mean value of the ratio of the fourth signal to the third signal is in a range from 50 to 300 values.

* * * * *

UNITED STATES PATENT AND TRADEMARK OFFICE
CERTIFICATE OF CORRECTION

PATENT NO. : 6,658,359 B2
DATED : December 2, 2003
INVENTOR(S) : Hubrich et al.

It is certified that error appears in the above-identified patent and that said Letters Patent is hereby corrected as shown below:

<u>Title page,</u>
Item [57], ABSTRACT,
Cancel the Abstract and replace to read:

-- A method for determining the viscosity of an operating liquid of an internal combustion engine of a vehicle involves constantly measuring the level of the operating liquid and the variation of the transverse acceleration of the vehicle, to determine the viscosity of the operating liquid from the variation against time of the two signal curves. The two signals are filtered and then a mean value of a ratio thereof gives the viscosity. Sensor signals which are already available from proven series-production sensor arrangements are combined to also determine the viscosity as an additional parameter. The computations needed for this are performed by standard control units.--.

Signed and Sealed this

Twenty-seventh Day of April, 2004

JON W. DUDAS
*Acting Director of the United States Patent and Trademark Office*